US010953096B2

(12) United States Patent
Takita et al.

(10) Patent No.: US 10,953,096 B2
(45) Date of Patent: Mar. 23, 2021

(54) TRANSDERMAL ABSORPTION PREPARATION PRECURSOR

(71) Applicant: Nitto Denko Corporation, Ibaraki (JP)

(72) Inventors: Tomohito Takita, Ibaraki (JP); Kaiji Fujiwara, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 0 days.

(21) Appl. No.: 15/935,568

(22) Filed: Mar. 26, 2018

(65) Prior Publication Data

US 2018/0311363 A1 Nov. 1, 2018

(30) Foreign Application Priority Data

Apr. 28, 2017 (JP) .............................. JP2017-090695
Feb. 6, 2018 (JP) .............................. JP2018-019319

(51) Int. Cl.
| | | |
|---|---|---|
| *A61K 9/70* | (2006.01) | |
| *A61K 47/32* | (2006.01) | |
| *A61K 31/135* | (2006.01) | |

(52) U.S. Cl.
CPC .............. *A61K 47/32* (2013.01); *A61K 9/703* (2013.01); *A61K 9/7038* (2013.01); *A61K 9/7061* (2013.01); *A61K 9/7084* (2013.01); *A61K 31/135* (2013.01)

(58) Field of Classification Search
CPC ...... A61K 9/70; A61K 9/7007; A61K 9/7015; A61K 9/7023; A61K 9/7046; A61K 9/7084; A61K 9/7092
See application file for complete search history.

(56) References Cited

U.S. PATENT DOCUMENTS

| | | | | |
|---|---|---|---|---|
| 6,548,727 | B1 * | 4/2003 | Swenson | .................. A61L 15/26 602/41 |
| 2008/0020007 | A1 | 1/2008 | Zang | |
| 2009/0216169 | A1 * | 8/2009 | Hansen | .................. A61F 15/001 602/48 |

FOREIGN PATENT DOCUMENTS

| | | |
|---|---|---|
| GB | 2485637 A | 5/2012 |
| JP | 2005-010529 A | 1/2005 |
| JP | 2006-034653 A | 2/2006 |
| JP | 2008-525334 A | 7/2008 |
| JP | 2014-215359 A | 11/2014 |
| JP | 2014215359 A * | 11/2014 |
| KR | 10-1992-0021137 A | 12/1992 |
| KR | 10-2009-0039724 A | 4/2009 |
| KR | 10-2011-0063515 A | 6/2011 |
| WO | WO 1991/003998 A1 | 4/1991 |
| WO | WO 2001/026705 A2 | 4/2001 |
| WO | WO 2001/026705 A3 | 4/2001 |
| WO | WO 2005/025549 A2 | 3/2005 |
| WO | WO-2005025549 A2 * | 3/2005 ............. A61K 9/703 |
| WO | WO 2005/081964 A2 | 9/2005 |
| WO | WO 2010/027468 A1 | 3/2010 |
| WO | WO 2012/069820 A1 | 5/2012 |

OTHER PUBLICATIONS

Taiwanese Patent Office, Office Action in Taiwanese Patent Application No. 107110276 (dated Jan. 31, 2019).
Japanese Patent Office, Notice of Reasons for Refusal in Japanese Patent Application No. 2018-019319 (dated Oct. 16, 2018).
European Patent Office, Extended European Search Report in European Patent Application No. 18164008.7 (dated Aug. 7, 2018).
Japanese Patent Office, Reconsideration Report by Examiner before Appeal in Japanese Patent Application No. 2018-019319 (dated Oct. 9, 2019).
Japanese Patent Office, Notice of Termination of Reconsideration by Examiners before Appeal Proceedings in Japanese Patent Application No. 2018-019319 (dated Oct. 11, 2019).
Japanese Patent Office, Notice of Reasons for Refusal in Japanese Patent Application No. 2018-019319 (dated Jul. 7, 2020).
China National Intellectual Property Administration, First Office Action and Search Report in Chinese Patent Application No. 201810253303.2 (dated Nov. 19, 2020).

* cited by examiner

*Primary Examiner* — Micah Paul Young
(74) *Attorney, Agent, or Firm* — Leydig, Voit & Mayer, Ltd.

(57) ABSTRACT

A transdermal absorption preparation precursor 50 containing a release liner 10 containing one first valley fold part 1, one or two first mountain fold parts 2, and a first base line L1 and a second base line L2 on one side and the other side apart from the first valley fold part 1 as a line of demarcation and at an approximately equal distance from the first valley fold part 1, wherein at least one of the first base line L1 and the second base line L2 is a fold line of the first mountain fold part 2, and a drug-containing layer 3 having a center line laid on the first base line L1 and an adhesive layer 4 having a center line laid on the second base line L2 on the release liner 10.

18 Claims, 6 Drawing Sheets

(A)

(B)

(C)

(D)

(E)

(A)

(B)

(A)

(B)

Fig. 4-3
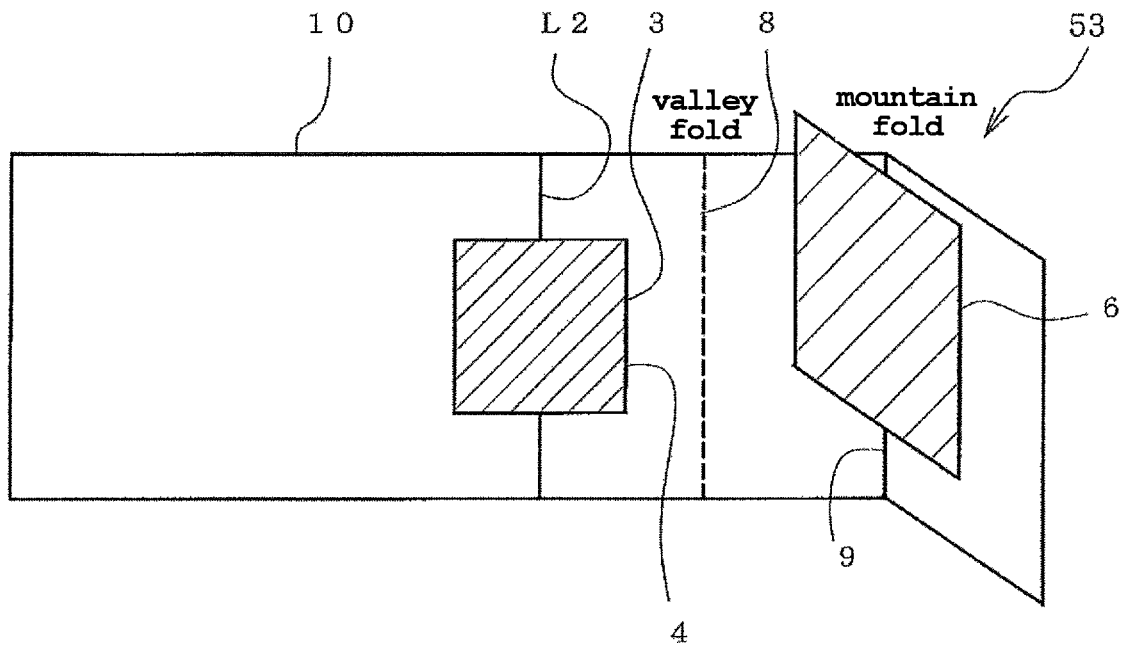
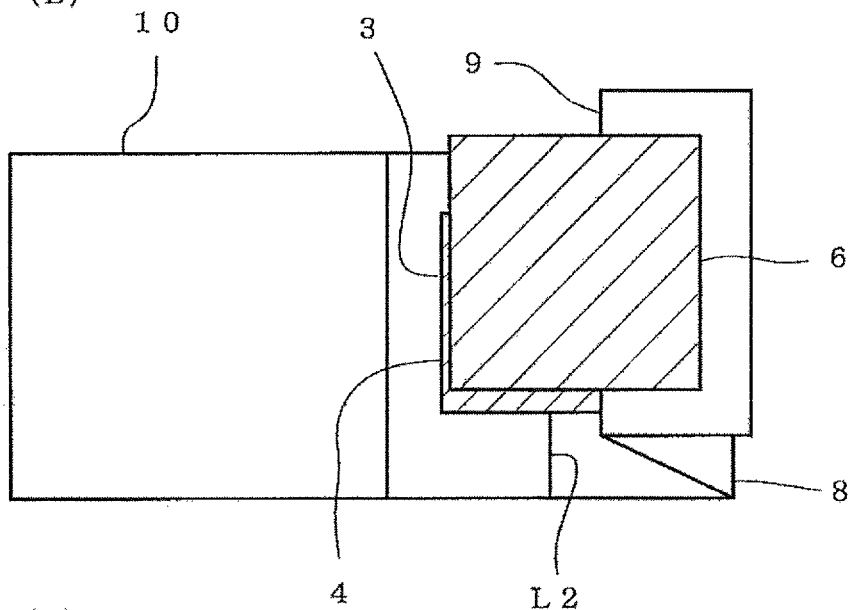
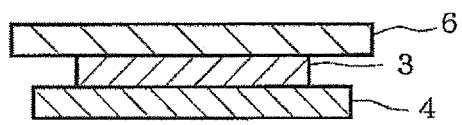

TRANSDERMAL ABSORPTION PREPARATION PRECURSOR

TECHNICAL FIELD OF THE INVENTION

The present invention relates to a transdermal absorption preparation precursor for obtaining, for example, a transdermal absorption preparation simultaneously achieving preservation stability of a drug and skin permeability of the drug at high levels.

BACKGROUND OF THE INVENTION

Transdermal absorption preparations not only intend to treat lesions on the skin surface or in the tissues directly under skin application site by topical absorption of the drug, but are also used as preparations expected to act not only on the skin and nearby tissues but also systemically by being taken into the blood from subcutaneous blood vessels. They have been recognized as one of the drug delivery systems.

Transdermal absorption preparations sometimes contain a drug penetration enhancer (skin permeation enhancer). In this case, the contained penetration enhancer may react with the drug to cause a drug stability problem during storage of the transdermal absorption preparation. In addition, when the drug contained in the transdermal absorption preparation is in an amorphous state, the presence of a certain kind of additive makes it difficult for the drug to maintain the amorphous state during storage of the transdermal absorption preparation. As a result, the drug is crystallized to possibly cause problems such as inconsistent skin permeability, poor appearance and the like.

To solve such problems, JP-A-2008-525334 proposes a transdermal therapeutic system in which a verum compartment containing an active substance in a fully crystallized form (coagulated solid state) and an enhancer compartment containing at least one liquid penetration enhancer are separately preserved, and these compartments are combined at the time of application to the human skin, whereby the active substance (drug) is dissolved by the penetration enhancer and delivered in an oversaturated state.

SUMMARY OF THE INVENTION

To be specific, in the transdermal therapeutic system of JP-A-2008-525334, a sheet (verum compartment) having an adhesive layer containing an active substance (drug) formed on a support such as plastic film or the like is laminated on a film impermeable to the active substance and preserved, a back (enhancer compartment) conferred with adhesiveness on its outer surface and storing a liquid penetration enhancer is produced and preserved, and the two are adhered when in use via a plastic film (control film) that controls permeability of the liquid penetration enhancer to construct a multi-layer structure (see FIG. 1a-1b) and applied to the skin. Therefore, the two compartments need to be produced separately. In addition, to provide a system enabling delivery of the object active substance in an oversaturated state, it is necessary to construct the system such that the laminating position and closely adhered state of the both compartments in the multi-layer structure would be appropriate positions and appropriate state. When a user (patient) him/herself constructs the system, the operation may be often extremely complicated and accurate construction may be often difficult.

The present invention has been made in view of the above-mentioned situation and aims to provide a transdermal absorption preparation precursor containing constituent components feared to cause an adverse influence when preserved in a mixed state or contact state, wherein the constituent components can be preserved in a mutually separated state and a transdermal absorption preparation having a given laminate structure can be conveniently obtained when in use.

The present inventors have conducted intensive studies in an attempt to solve the aforementioned problems and found that, by separately arranging, on a release liner having a valley fold part and a mountain fold part formed at a given distance, two layers to be directly laminated in a given transdermal absorption preparation to be produced, the transdermal absorption preparation constituent components feared to mutually cause an adverse influence can be preserved in a mutually separated state, and a transdermal absorption preparation having a given laminate structure can be constructed with ease without producing a positional deviation of each layer by simple valley folding and mountain folding of the release liner by a user (patient) when in use, which resulted in the completion of the present invention.

Therefore, the present invention provides the following.

[1] A transdermal absorption preparation precursor comprising a release liner, a first layer formed on the release liner and a second layer formed on the release liner, the release liner comprising one first valley fold part, one or two first mountain fold parts, and a first base line and a second base line on one side and the other side apart from the first valley fold part as a line of demarcation and at an approximately equal distance from the first valley fold part, wherein at least one of the first base line and the second base line is a fold line of the first mountain fold part, the first layer having a planar shape being disposed on the release liner such that the center line of the plane is positioned on the first base line, and the second layer having a planar shape being disposed on the release liner such that the center line of the plane is positioned on the second base line, wherein the first layer and/or the second layer comprise(s) a drug.

[2] The transdermal absorption preparation precursor of the above-mentioned [1], wherein one of the first layer and the second layer is a drug-containing layer and the other is an adhesive layer.

[3] The transdermal absorption preparation precursor of the above-mentioned [2], wherein the adhesive layer comprises an additive.

[4] The transdermal absorption preparation precursor of the above-mentioned [2] or [3], wherein a control layer is laminated on the adhesive layer.

[5] The transdermal absorption preparation precursor of the above-mentioned [2] or [3], wherein the adhesive layer comprises a drug.

[6] The transdermal absorption preparation precursor of any of the above-mentioned [2] to [5], wherein a substrate layer and/or a cover layer are/is laminated on the drug-containing layer.

[7] The transdermal absorption preparation precursor of any of the above-mentioned [1] to [5], further comprising a second valley fold part at a position opposite from the first valley fold part with the second base line of the release liner as a line of demarcation;

a second mountain fold part at a position opposite from the second base line with the second valley fold part as a line of demarcation; and a third layer having a planar shape and disposed on the release liner such that the center line of the plane is positioned on a fold line of the second mountain fold part, wherein the distance between the second valley fold part and the second base line is approximately equal to the distance between the second mountain fold part and the second valley fold part.

[8] The transdermal absorption preparation precursor of the above-mentioned [7], wherein the third layer is a cover layer.

[9] The transdermal absorption preparation precursor of the above-mentioned [7], wherein the third layer is a drug-containing layer.

In the transdermal absorption preparation precursor of the present invention, the "center line" means a line that passes through the center point of the area of a layer surface (i.e., plane) when viewed from vertically upward and divides the area into approximately equal two areas.

In addition, "on the release liner" basically means on a face subjected to a release treatment of a release liner.

Furthermore, the "base line" of the "release liner" when the base line is not the fold line of the mountain fold part refers to a straight line recognizable by at least vision or touch, which is imparted by coloration, embossing and the like on the release liner.

According to the transdermal absorption preparation precursor of the present invention, since two layers to be directly laminated to constitute the transdermal absorption preparation can be separately stored, which in turn enables storage of a compound reactive with the drug in a layer different from the drug layer. Thus, stability of the drug can be maintained during the storage. When a drug is administered using a transdermal absorption preparation, a transdermal absorption preparation having a given laminate structure can be constructed with ease without producing a positional deviation in the planar direction of each layer by simple mountain folding a mountain fold part formed on the release liner and valley folding a valley fold part formed on the release liner. Therefore, for example, at the time of drug administration using a transdermal absorption preparation, a user (patient) him/herself can easily and certainly construct a transdermal absorption preparation capable of affording given properties and apply to the skin.

BRIEF DESCRIPTION OF THE DRAWINGS

FIG. 4-1(A) and FIG. 4-1(B) are schematic drawings of one embodiment of the fourth embodiment of the transdermal absorption preparation precursor of the present invention.

FIG. 4-2(A) and FIG. 4-2(B) are schematic drawings of one embodiment of the fourth embodiment of the transdermal absorption preparation precursor of the present invention.

FIG. 4-3(A) and FIG. 4-3(B) are schematic drawings of one embodiment of the fourth embodiment of the transdermal absorption preparation precursor of the present invention, and FIG. 4-3(C) is a schematic drawing of a transdermal absorption preparation constructed using the transdermal absorption preparation precursor. In the Figures, 1 is the first valley fold part, 2 is the first mountain fold part, 3 is a drug-containing layer, 4 is an adhesive layer, L1 is the first base line, L2 is the second base line, 10 is a release liner, and 50-53 are transdermal absorption preparation precursors.

DETAILED DESCRIPTION OF THE INVENTION

The present invention is explained in the following by referring to preferable embodiments. Such detailed explanations and particular examples are mere exemplifications and do not intend to limit the present invention, applications thereof or use. In the following explanations, "approximately equal distance" and "distance is approximately equal" means that two distances should be set equal in light of the object of the present invention and two distances may be somewhat different as long as the object of the present invention can be achieved.

1. The First Embodiment

Figure 1:
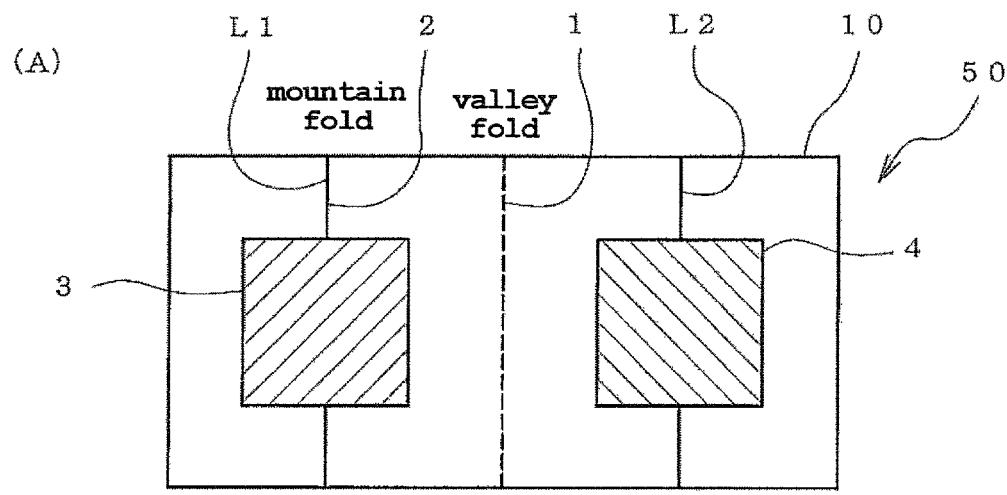
FIG. 1(A)-FIG. 1(C) are schematic drawings of one embodiment of the first embodiment of the transdermal absorption preparation precursor of the present invention.
FIG. 1(D) is a schematic sectional drawing of a transdermal absorption preparation constructed using the transdermal absorption preparation precursor.
Figure 1:
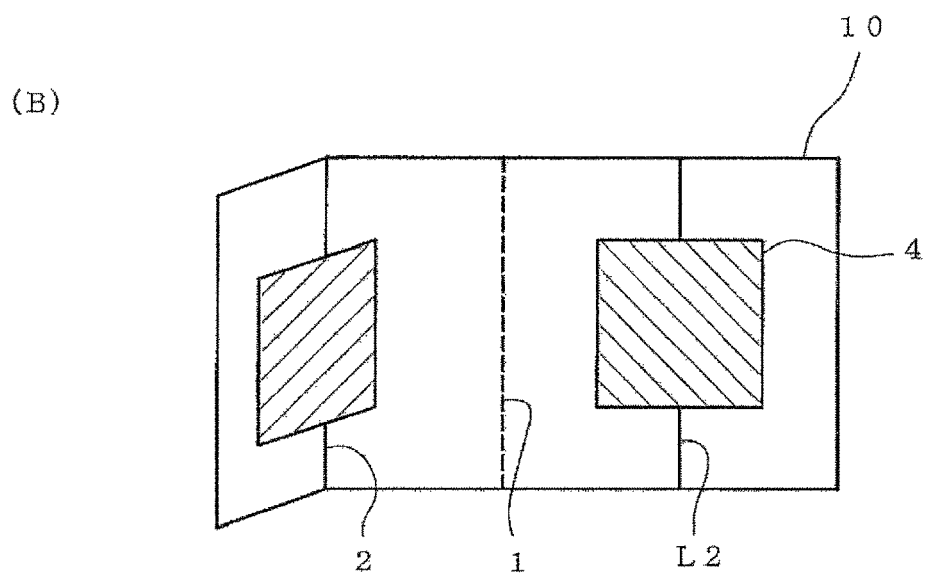
Figure 1:
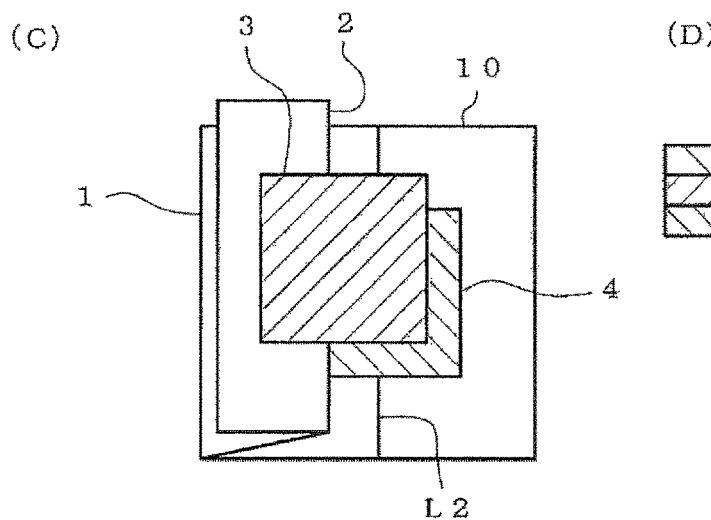
Figure 1:

FIG. 1 is a schematic drawing of one embodiment of the first embodiment of the transdermal absorption preparation precursor of the present invention.

The transdermal absorption preparation precursor 50 of this embodiment has a release liner 10 comprising one first valley fold part 1 and one first mountain fold part 2, a first base line L1 and a second base line L2 on one side and the other side apart from the first valley fold part 1 as a line of demarcation and at an approximately equal distance from the first valley fold part 1, wherein a fold line of the first mountain fold part 2 is placed on the first base line L1. In addition, a drug-containing layer 3 having a planar shape is disposed on the release liner such that the center line of the plane is positioned on the first base line L1, and an adhesive layer 4 having a planar shape is disposed on the release liner 10 such that the center line of the plane is positioned on the second base line L2 (FIG. 1(A)). The second base line L2 is not a fold line of the mountain fold part but a straight line recognizable by at least vision or touch, which is imparted by coloration, embossing and the like on the release liner.

The transdermal absorption preparation precursor 50 of the first embodiment can separately preserve a drug-containing layer 3 and an adhesive layer 4. When the transdermal absorption preparation is applied to the skin, the first mountain fold part 2 is mountain folded (FIG. 1(B)), the first valley fold part 1 is valley folded (FIG. 1(C)), and the drug-containing layer 3 is laid (aligned) on the adhesive layer 4 while detaching the release liner 10 from the drug-containing layer 3, whereby a transdermal absorption preparation having a laminate structure of drug-containing layer 3/adhesive layer 4 on the release liner 10 is completed.

After complete detachment of the release liner 10 from the drug-containing layer 3, the substrate layer 5 can be laminated on the drug-containing layer 3, whereby a transdermal absorption preparation having a laminate structure of substrate layer 5/drug-containing layer 3/adhesive layer 4 (FIG. 1(D)) can be obtained. In addition, when the substrate layer 5 is previously laminated on the drug-containing layer 3 arranged on the release liner 10, the first mountain fold part 2 is mountain folded, the first valley fold part 1 is valley folded, and the drug-containing layer 3 is laid (aligned) on the adhesive layer 4 while detaching the release liner 10 from the drug-containing layer 3, whereby a transdermal absorption preparation having a laminate structure of substrate layer 5/drug-containing layer 3/adhesive layer 4 (FIG. 1(D)) can be obtained.

Before the first mountain fold part 2 of the release liner 10 is mountain folded, i.e., during the storage period of the transdermal absorption preparation precursor, it is preferable to form a protective layer (release liner for protection) (not shown) on the outermost surface of the drug-containing layer 3 and the adhesive layer 4. That is, before completion of the transdermal absorption preparation and application thereof to the skin, the drug-containing layer 3 and the adhesive layer 4 are preferably protected by a protective layer (release liner for protection).

In the example of FIG. 1 (transdermal absorption preparation precursor 50), the second base line L2 is a straight line imparted on the release liner 10 by coloration, embossing or the like. Instead of the straight line, the first mountain fold part 2 may be formed such that the fold line thereof is laid on the second base line L2. In this way, the release liner 10 is easily detached from the transdermal absorption preparation completed on the release liner 10 (that is, after the state of FIG. 1(C), the release liner 10 is easily detached), and the transdermal absorption preparation can be more easily applied to the skin.

Release Liner

In the transdermal absorption preparation precursor of the present invention, the release liner 10 is not particularly limited, and a plastic film of polyester (e.g., poly(ethylene terephthalate) etc.), polyvinyl chloride, polyvinylidene chloride and the like, paper such as quality paper, glassine and the like, a laminate film of two or more kinds selected from these and the like, each of which is subjected to a release treatment by applying a silicone-based release agent, a fluorine-based release agent or the like, is used. The release liner 10 is subjected to a given bending processing to form a valley fold part and a mountain fold part. The sheet can be bent by a known method, and examples thereof include the methods described in JP-A-6-166463, JP-A-2006-282314 and the like. Bending of a sheet is processing to confer a folding habit (bending habit) to the sheet. Generally, the sheet after processing has a fold line to be the top line of the mountain fold part and a fold line to be the bottom line of the valley fold part.

While the thickness of the release liner 10 is not particularly limited, it is generally about 10-200 μm, preferably about 25-100 μm, from the aspects of the easiness of the processing for forming a valley fold part and a mountain fold part, the easiness of the mountain folding operation and valley folding operation to complete a transdermal absorption preparation on a release liner, shape stability of a release liner during storage of a transdermal absorption preparation precursor and the like.

The planar shape of the release liner 10 generally preferably rectangle shown in FIG. 1(A) in view of the easiness of the valley folding operation and mountain folding operation, but the shape is not limited thereto. The plane area of the release liner 10 is determined in consideration of the plane area of the transdermal absorption preparation to be produced and the number of the layers constituting the transdermal absorption preparation and the like. For example, when a release liner has a rectangular planar shape, it is preferably about 30-400 $cm^2$, but the plane area is not limited thereto.

The release liner 10 may have a valley fold part and a mountain fold part which are softer than other parts or have a smaller thickness to facilitate the valley folding operation of the valley fold part and the mountain folding operation of the mountain fold part.

In the release liner 10, the distance between the first valley fold part 1 and the first base line L1, and the distance between the first valley fold part 1 and the second base line L2, which are approximately equal (see FIG. 1(A)) are determined according to the plane area of the transdermal absorption preparation to be produced and is not particularly limited. It is generally selected from 2-20 cm.

Drug-Containing Layer

In the transdermal absorption preparation precursor of the present invention, the drug-containing layer 3 generally contains a drug and a matrix polymer as essential components. While the matrix polymer is not particularly limited, when, for example, the drug-containing layer is a layer containing a drug in an amorphous state, the matrix polymer is preferably a polymer having a glass transition temperature of 30° C.-200° C. A polymer having a glass transition temperature of 30° C.-200° C. is rigid, suppresses movement and coagulation of a drug in the drug-containing layer, and suppresses crystallization of a drug present in an amorphous state. The polymer having a glass transition temperature of 30° C.-200° C. preferably has a glass transition temperature of 50° C.-200° C., more preferably 60° C. -180° C.

The "glass transition temperature" here means a temperature at which the rigidity and viscosity decrease rapidly and the flowability increases when an amorphous solid is heated. The glass transition temperature of a polymer can be measured by differential scanning calorimetry (DSC) and the like.

Examples of the polymer having a glass transition temperature of 30° C.-200° C. include cellulose derivatives such as hydroxypropylmethylcellulose, hydroxypropylmethylcellulose phthalate, hydroxypropylcellulose, acetyl cellulose and the like; acrylic polymers such as acrylic resin, methacrylic acid-methyl methacrylate copolymer (methacrylic acid copolymer S ("EUDRAGIT S100"), methacrylic acid copolymer L ("EUDRAGIT L100"), manufactured by Evonik Rohm GmbH), methacrylic acid-ethyl acrylate copolymer (dried methacrylic acid copolymer LD ("EUDRAGIT L100-55", manufactured by Evonik Rohm GmbH)), methyl methacrylate-butyl methacrylate-dimethylaminoethyl methacrylate copolymer (aminoalkyl methacrylate copolymer E ("EUDRAGIT EPO", manufactured by Evonik Rohm GmbH)), methyl methacrylate-ethyl acrylate-chlorotrimethylammonioethyl methacrylate copolymer (ammonioalkyl methacrylate copolymer ("EUDRAGIT RSPO", EUDRAGIT RLPO", manufactured by Evonik Rohm GmbH)), ethyl acrylate-methyl methacrylate copolymer (ethyl acrylate-methyl methacrylate copolymer dispersion solution ("EUDRAGIT NE30D", manufactured by Evonik Rohm GmbH)) and the like; polyvinylpyrrolidone; vinylpyrrolidone-vinyl acetate copolymer; polycarbonate; cycloolefin copolymer; polyvinyl caprolactam-polyvinyl acetate-polyethylene glycol graft copolymer ("Soluplus"), manufactured by BASF); poly(vinyl alcohol); polyvinyl acetate and the like. One or more kinds thereof can be used.

The drug to be contained in the drug-containing layer 3 is not particularly limited, and a drug that can be administered to mammals such as human and the like through the skin thereof, namely, a transdermally absorbable drug, is preferable. Specific examples of such drug include general anesthetic, antipsychotic agent, antidepressant, mood stabilizer, psychostimulant, sleeping drug, antianxiety drug, antiepileptic, therapeutic drug for migrainea, antiemetic, anti-vertiginous drug, local anesthetic, muscle relaxant, autonomic drug, antiepileptic drug, therapeutic drug for Parkinson's disease, adrenal cortical steroid, non-steroidal antiinflammatory agent, analgesic antipyretic drug, anti-dementia drug, antirheumatic drug, anti-histamine drug, antiallergic agent, cardiotonic drug, antiarrhythmic drug, diuretic, depressor, vasoconstrictor, vasodilator, therapeutic drug for angina pectoris, anapnoic, bronchodilator, therapeutic drug for bronchial asthma, antitussive, expectorant, hormone drug, hematopoietic drug, hemostat, antithrombotic, therapeutic drug for gout-hyperuricemia, therapeutic drug for diabetes, a therapeutic drug for hyperlipidemia, antitumor drug, immunosuppressant, antibiotic, chemotherapy drug, antifungal drug, antiviral drug, antiparasitic agent, narcotic, quit-smoking drug and the like.

While the content of a drug in the drug-containing layer 3 varies depending on the kind of the drug, the age, sex, symptom of patients to whom the transdermal absorption preparation is used, and the like, it is generally 30-95 wt %, preferably 50-90 wt %, of the whole drug-containing layer 3.

The drug-containing layer 3 can contain additives such as organic acids such as acetic acid, lactic acid, octanoic acid, levulinic acid, oleic acid, decanoic acid, citric acid, fumaric acid, maleic acid and the like; organic bases such as monoethanolamine, diethanolamine, triethanolamine, diisopropanolamine, triisopropanolamine, pyridine, arginine and the like; plant-derived fats and oils such as olive oil, castor oil, coconut oil and the like; animal-derived fats and oils such as liquid lanolin and the like; organic solvents such as dimethyldecylsulfoxide, methyloctylsulfoxide, dimethyl sulfoxide, dimethylformamide, dimethylacetamide, dimethyllauryl amide, methylpyrrolidone, dodecylpyrrolidone and the like; surfactants such as polyoxyethylene sorbitan fatty acid ester, sorbitan fatty acid ester, polyoxyethylene fatty acid ester and the like; plasticizers such as diisopropyl adipate, phthalate, diethyl sebacate and the like; hydrocarbons such as squalane, liquid paraffin and the like; fatty acid esters such as ethyl oleate, isopropyl palmitate, octyl palmitate, isopropyl myristate, isotridecyl myristate, ethyl laurate and the like; polyhydric alcohol-fatty acid esters such as glycerol-fatty acid ester, propylene glycol-fatty acid ester and the like; linear aliphatic alcohols such as 1-dodecanol, 1-tetradecanol, 1-hexadecanol and the like; branched chain aliphatic alcohols such as 2-hexyl-1-decanol, 2-octyl-1-dodecanol, 2-hexyl-1-tetradecanol and the like; and the like. One kind of these additives may be used alone or two or more kinds thereof may be used in combination.

The drug-containing layer 3 has a planar shape. That is, it is present in an island shape on the surface of a release liner (release-treated surface). The planar shape and plane area of the drug-containing layer 3 follow the planar shape (e.g., approximate square, approximate rectangle, ellipse, circular shape etc.) and plane area of a given transdermal absorption preparation to be produced. Therefore, the plane area is generally selected from the range of 4-100 $cm^2$, though not limited thereto. The thickness of the drug-containing layer 3 is appropriately determined according to the kind of the drug to be contained and the like and is not particularly limited. It is generally 10-300 μm, preferably 50-200 μm.

Adhesive Layer

The adhesive layer 4 in the transdermal absorption preparation precursor of the present invention is a layer for adhering the transdermal absorption preparation to the skin. It contains a pressure-sensitive adhesive polymer as a main component and shows skin adhesiveness at ambient temperature (25° C.)

The pressure-sensitive adhesive polymer is not particularly limited and examples thereof include acrylic polymers including (meth)acrylate-based polymer; rubber-based polymers such as styrene-isoprene-styrene block copolymer, styrene-butadiene-styrene block copolymer, polyisoprene, polyisobutylene, polybutadiene and the like; silicone-based polymers such as silicone rubber, dimethylsiloxane base, diphenylsiloxane base and the like; vinyl ether-based polymers such as poly(vinyl methyl ether), poly(vinyl ethyl ether), poly(vinyl isobutyl ether) and the like; vinyl ester-based polymers such as vinyl acetate-ethylene copolymer and the like; ester-based polymers composed of a carboxylic acid component such as dimethyl terephthalate, dimethyl isophthalate, dimethyl phthalate or the like and a polyhydric alcohol component such as ethylene glycol or the like, and the like.

When a rubber-based polymer is used as the pressure-sensitive adhesive polymer, the adhesive layer preferably further contains a tackifier to improve skin adhesiveness of the adhesive layer at ambient temperature. Examples of the tackifier include petroleum resins (e.g., aromatic petroleum resin, aliphatic petroleum resin etc.), terpene-based resins, rosin resins, coumaroneinden resins, styrene-based resins (e.g., styrene resin, poly(α-methylstyrene) etc.), hydrogenated petroleum resins (e.g., alicyclic saturated hydrocarbon resin etc.) and the like. The amount of the tackifier is generally 33-300 wt %, preferably 50-200 wt %, of the total weight of the rubber-based polymer.

As an additive other than the tackifier that can be contained in the adhesive layer 4, a skin permeation enhancer that improves diffusibility, in the adhesive layer, of a drug penetrating from the drug-containing layer 3 when the drug-containing layer 3 is in a laminated state, and promotes skin permeability of the drug can be mentioned. Also, excipient, crosslinking agent, plasticizer, antioxidant, preservative and the like can be recited.

Examples of the skin permeation enhancer include organic acids such as acetic acid, lactic acid, octanoic acid, levulinic acid, oleic acid, decanoic acid, citric acid, fumaric acid, maleic acid and the like; organic bases such as monoethanolamine, diethanolamine, triethanolamine, diisopropanolamine, triisopropanolamine, pyridine, arginine and the like; plant-derived fats and oils such as olive oil, castor oil, coconut oil and the like; animal-derived fats and oils such as liquid lanolin and the like; organic solvents such as dimethyldecylsulfoxide, methyloctylsulfoxide, dimethyl sulfoxide, dimethylformamide, dimethylacetamide, dimethyllauryl amide, methylpyrrolidone, dodecylpyrrolidone and the like; surfactants such as polyoxyethylene sorbitan fatty acid ester, sorbitan fatty acid ester, polyoxyethylene fatty acid ester and the like; plasticizers such as diisopropyl adipate, phthalate, diethyl sebacate and the like; hydrocarbons such as squalane, liquid paraffin and the like; fatty acid esters such as ethyl oleate, isopropyl palmitate, octyl palmitate, isopropyl myristate, isotridecyl myristate, ethyl laurate and the like; polyhydric alcohol-fatty acid esters such as glycerol-fatty acid ester, propylene glycol-fatty acid ester and the like; linear aliphatic alcohols such as 1-dodecanol, 1-tetradecanol, 1-hexadecanol and the like; branched chain aliphatic alcohols such as 2-hexyl-1-decanol, 2-octyl-1-dodecanol, 2-hexyl-1-tetradecanol and the like; and the like.

One or more kinds of the skin permeation enhancer are used and the content of the skin permeation enhancer in an adhesive layer is not particularly limited. It is generally about 10-70wt %, preferably 20-40 wt %, of the whole adhesive layer. When the content is less than 10 wt %, a sufficient skin permeability enhancing effect on a drug may not be achieved. Conversely, when the content exceeds 70 wt %, the skin permeation enhancer may bloom on the surface of the adhesive layer.

The adhesive layer 4 may be subjected to physical crosslinking by radiation such as UV radiation, electron beam radiation or the like, or a chemical crosslinking treatment using various a crosslinking agent such as an isocyanate-based compound such as trifunctional isocyanate or the like, organic peroxide, organic metal salt, metal alcholate, metal chelate compound, polyfunctional compound (polyfunctional external crosslinking agent, polyfunctional internal crosslinking monomers such as diacrylate, dimethacrylate and the like) or the like to give a crosslinked adhesive layer.

The adhesive layer 4 may contain a drug. The drug may be the same as or different from the drug contained in the drug-containing layer 3. For example, when a drug contained in the drug-containing layer 3 is not sufficient to ensure the dose, the same drug may be contained in the adhesive layer 4 to ensure a sufficient dose. When two drugs that are feared to cause an interaction between them or denaturation thereof when they are contained in the same layer are used, the transdermal absorption preparation precursor of the present invention can preserve such two drugs without interaction or denaturation by containing the drugs separately in the drug-containing layer 3 and the adhesive layer 4. When they are actually administered, a transdermal absorption preparation is completed on a release liner (i.e., laminating drug-containing layer 3 on adhesive layer 4) and applied to the skin, whereby the two drugs can be administered simultaneously.

While the content of the drug in the adhesive layer 4 is appropriately determined according to the kind of the drug, administration object, content of the drug in the drug-containing layer 3 and the like, and is not particularly limited. It is generally about 1-40 wt % of the whole adhesive layer.

While the thickness of the adhesive layer 4 is appropriately determined according to the kind of the adhesive to be used for the adhesive layer and the like. It is generally 50-200 μm, preferably 50-100 μm. When it is less than 50 μm, adhesiveness to the skin may not be sufficiently exhibited. When it exceeds 200 μm, improvement of adhesiveness will cease and the material cost may become higher.

Substrate Layer

The substrate layer 5 in the transdermal absorption preparation precursor of the present invention is a layer that retains the drug-containing layer as a support in the completed transdermal absorption preparation. The material of the substrate layer is not particularly limited, and a preferable material is one that does not allow a drug contained in the drug-containing layer to pass through the substrate layer and get lost from the back face to decrease the content, namely, one constituted of a material impermeable to the drug. Examples thereof include single films of polyester-based resins such as poly(ethylene terephthalate) and the like; polyamide-based resins such as nylon and the like; olefin-based resins such as polyethylene, polypropylene and the like; vinyl-based resins such as ethylene-vinyl acetate copolymer, polyvinyl chloride, polyvinylidene chloride, ionomer resin and the like; acrylic resins such as ethylene-ethyl acrylate copolymer and the like; fluorocarbon resins such as polytetrafluoroethylene and the like; metal foil and the like, and these laminate films and the like. The thickness of the substrate layer is generally 10 μm-200 μm, preferably 15 μm-150 μm, more preferably 20 μm-100 μm.

To improve adhesiveness (anchor property) between the substrate layer 5 and the drug-containing layer 3, the substrate is preferably a laminate film of a non-porous film made of the above-mentioned material and a porous film, and the porous film and the drug-containing layer are laminated to be adhered to each other. The aforementioned porous film is not particularly limited as long as the anchor property between the substrate layer and the drug-containing layer is improved. Examples thereof include paper, woven fabric, non-woven fabric, mechanically perforation-treated film and the like, particularly paper, woven fabric and non-woven fabric are preferable. The thickness of the porous film is preferably 10 μm-100 μm in consideration of the improvement of the anchor property and flexibility of the drug-containing layer. When woven fabric or non-woven fabric is used as a porous film, the amount thereof is preferably set to 3 g/m²-50 g/m², more preferably 5 g/m²-30 g/m², to improve anchor property.

Protective Layer (Release Liner for Protection)

The transdermal absorption preparation precursor of the present invention may have a protective layer (release liner for protection) to protect the drug-containing layer 3 and the adhesive layer 4. The protective layer (release liner for protection) is not particularly limited as long as sufficiently light release property from the drug-containing layer 3 and the adhesive layer 4 can be secured. Specific examples include plastic films of polyester, polyvinyl chloride, polyvinylidene chloride, poly(ethylene terephthalate) and the like, paper such as quality paper, glassine and the like, and laminate film of quality paper, glassine or the like and polyolefin, and the like, each of which underwent a release treatment by applying silicone resin, fluoro resin or the like. The thickness of the protective layer (release liner) is generally about 10-200 μm.

The planar shape of the adhesive layer 4, substrate layer and protective layer (release liner for protection) is basically the same as the planar shape (e.g., approximate square, approximate rectangle, ellipse, circular shape etc.) of the drug-containing layer 3. The size (plane area) thereof is also basically the same as that of the drug-containing layer 3. The adhesive layer 4, substrate layer 5 and protective layer (release liner for protection) may be somewhat larger than the drug-containing layer 3. That is, the size may be set to protrude by not more than about 20 mm from the periphery in the entire circumference of the drug-containing layer 3, but the protrusion length (dimension) is not limited thereto.

2. Second Embodiment

FIG. 2(A)-FIG. 2(C) are schematic drawings of one embodiment of the second embodiment of the transdermal absorption preparation precursor of the present invention, FIG. 2(D) is a schematic sectional drawing of a transdermal absorption preparation constructed using the transdermal absorption preparation precursor, and FIG. 2(E) is a schematic drawing of the transdermal absorption preparation of FIG. 2(D) when applied to the skin. In these Figures, the symbols same as those in FIG. 1(A)-FIG. 1(D) show the same or corresponding parts. Symbol 20 in FIG. 2(E) shows the skin surface.

The second embodiment of the transdermal absorption preparation precursor of the present invention is different from the first embodiment of the transdermal absorption preparation precursor 50 in that the cover layer 6 is laminated on the drug-containing layer 3.

Figure 2:
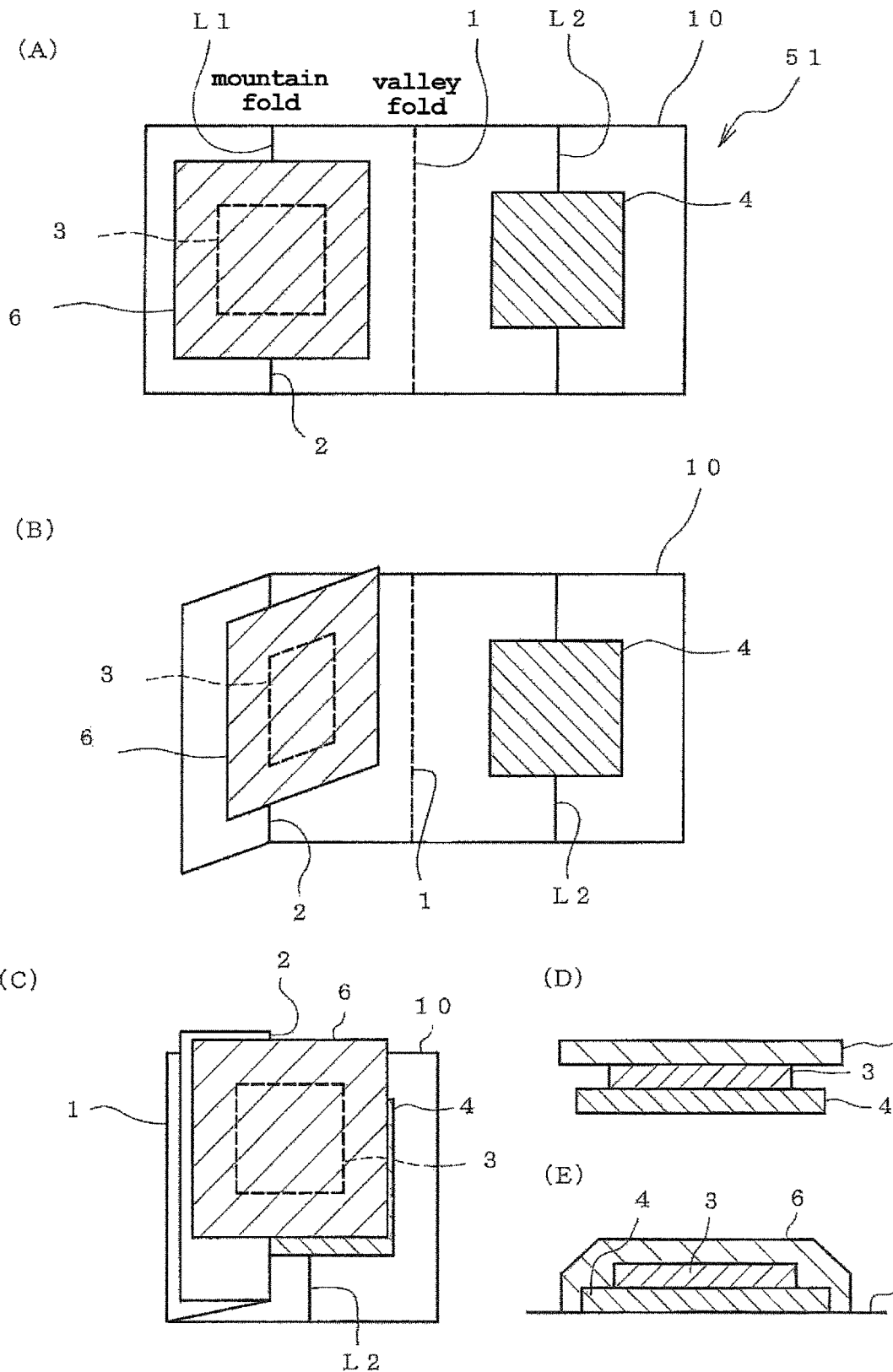
FIG. 2(A)-FIG. 2(C) are schematic drawings of one embodiment of the second embodiment of the transdermal absorption preparation precursor of the present invention.
FIG. 2(D) is a schematic sectional drawing of a transdermal absorption preparation constructed using the transdermal absorption preparation precursor.
FIG. 2(E) is a schematic drawing of the transdermal absorption preparation of FIG. 2(D) when applied to the skin.

In the example of FIG. 2 (transdermal absorption preparation precursor 51), the second base line L2 is a straight line imparted on the release liner 10 by coloration, embossing or the like. The second base line L2 may also be formed by the fold line of the first mountain fold part 2. In this way, the release liner 10 is easily detached from the transdermal absorption preparation completed on the release liner 10, and the transdermal absorption preparation can be more easily applied to the skin.

Cover Layer

As shown in the second embodiment of the transdermal absorption preparation precursor 51, a cover layer 6 may be laminated on the drug-containing layer 3 in the transdermal absorption preparation precursor of the present invention. The cover layer 6 may have the function of the substrate layer 5. Alternatively, the substrate layer 5 may be previously laminated on the drug-containing layer 3 and the cover layer 6 may be laminated on the substrate layer 5.

In the transdermal absorption preparation precursor of the present invention, the cover layer 6 is a layer for protecting the drug-containing layer 3. In FIG. 2(A), the cover layer 6 in a planar shape larger in size than the drug-containing layer 3 is formed as a sheet having a substantially square shape.

In the transdermal absorption preparation precursor of the present invention, the plane area of the cover layer 6 is not particularly limited as long as it can cover the drug-containing layer 3. For example, a size protruding by not less than 0.5 cm and not more than 5 cm from the periphery in the entire circumference of the drug-containing layer 3 is preferable.

The material of the cover layer 6 is basically the same as that of the substrate layer. As the cover layer 6, for example, a single film and laminate film of resin and these films laminated with woven fabric, non-woven fabric or the like can be used. Of these, one maintaining skin followability, that is, one easily expanding and/or contracting according to the elongation of the skin surface is preferable. For example, single films and laminate films made of one or more kinds of thermoplastic resins selected from the group consisting of poly(ethylene terephthalate), nylon, polyethylene, polypropylene, ethylene-vinyl acetate copolymer, polyvinyl chloride, polyvinylidene chloride, ionomer resin, ethylene-ethyl acrylate copolymer and polytetrafluoroethylene, and these films laminated with woven fabric or non-woven fabric are preferably used.

As a fiber constituting woven fabric or non-woven fabric, a resin fiber made of a thermoplastic resin or thermosetting resin is preferable. Specific examples thereof include fiber based on olefin resin such as polyethylene, polypropylene or the like, fiber based on polyester such as poly(ethylene terephthalate) or the like, fiber based on polyamide-based resin such as nylon or the like, fiber based on cellulose resin, and the like. Any one kind of these resin fibers may be used alone, or two or more kinds thereof may be used in combination.

The thickness of the cover layer 6 is not particularly limited and it is, for example, preferably 10-200 μm, more preferably 25-100 μm.

As shown in FIG. 2(E), when the transdermal absorption preparation is applied to the skin, the cover layer 6 is disposed to entirely cover the drug-containing layer 3 and the adhesive layer 4 on the skin surface 20. Therefore, generally, an adhesive for skin such as acrylic adhesive, rubber-based adhesive, silicone-based adhesive or the like is applied to at least the peripheral portion of the bottom surface of the cover layer 6 (surface in contact with drug-containing layer 3 or substrate layer 5).

Many through-holes penetrating the cover layer 6 in the thickness direction may or may not be formed.

3. Third Eembodiment

FIG. 3(A)-FIG. 3(C) are schematic drawings of one embodiment of the third embodiment of the transdermal absorption preparation precursor of the present invention, FIG. 3(D) is a schematic sectional drawing of a transdermal absorption preparation constructed using the transdermal absorption preparation precursor, and FIG. 3(E) is a schematic drawing of the transdermal absorption preparation of FIG. 3(D) when applied to the skin. In these Figures, the symbols same as those in FIG. 2(A)-FIG. 2(D) show the same or corresponding parts.

The third embodiment of the transdermal absorption preparation precursor is different from the second embodiment of the transdermal absorption preparation precursor 51 in that the control layer 7 is laminated on the adhesive layer 4.

Figure 3:
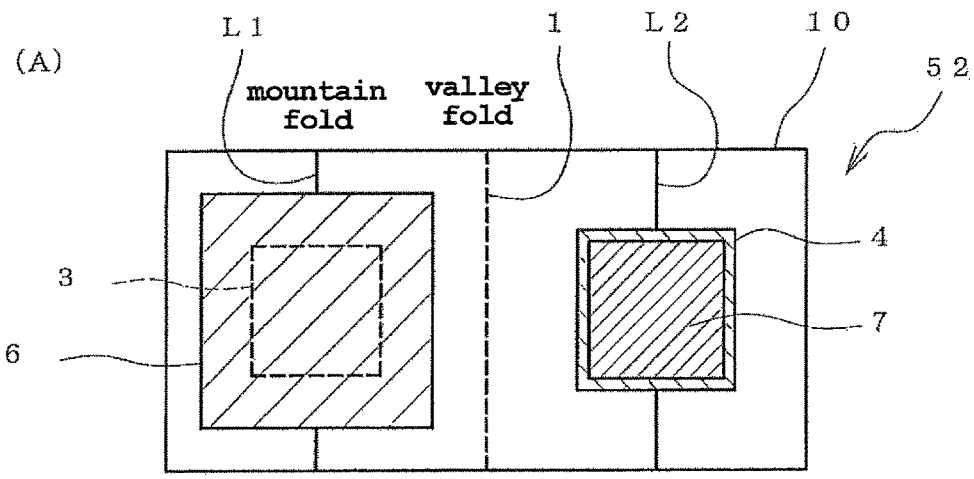
FIG. 3(A)-FIG. 3(C) are schematic drawings of one embodiment of the third embodiment of the transdermal absorption preparation precursor of the present invention.
FIG. 3(D) is a schematic sectional drawing of a transdermal absorption preparation constructed using the transdermal absorption preparation precursor.
FIG. 3(E) is a schematic drawing of the transdermal absorption preparation of FIG. 3(D) when applied to the skin.
Figure 3:
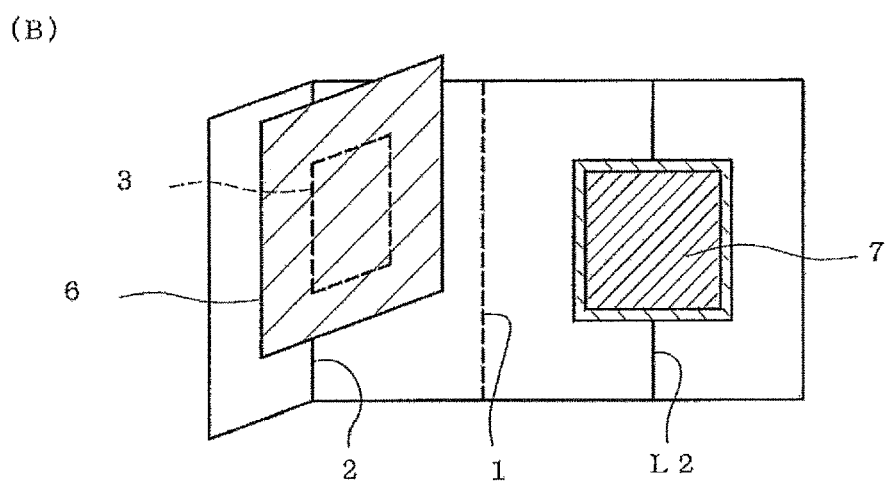
Figure 3:
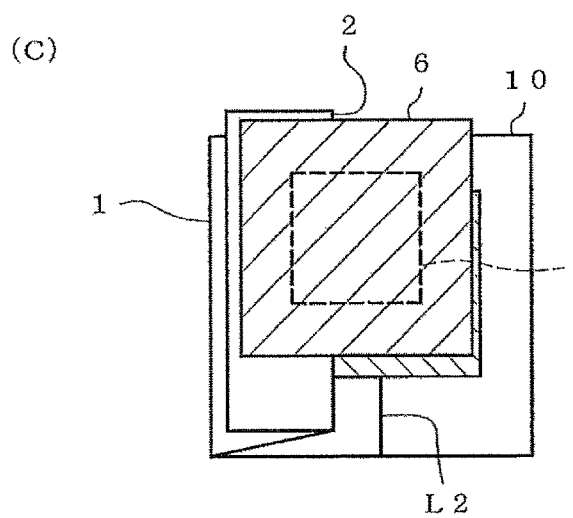
Figure 3:
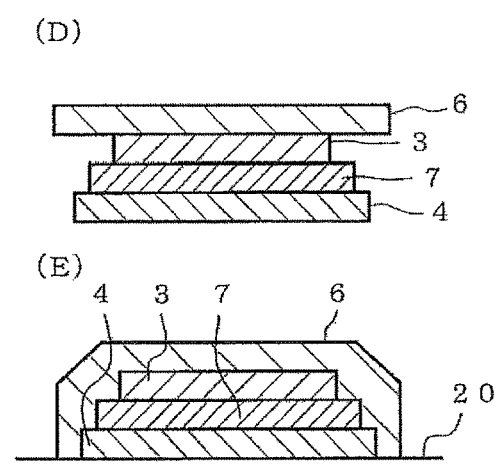

In the example of FIG. 3 (transdermal absorption preparation precursor 52), the second base line L2 is a straight line imparted on the release liner 10 by coloration, embossing or the like. Instead of the straight line, the first mountain fold part 2 having a fold line laid on the second base line L2 may also be formed. In this way, the release liner 10 is easily detached from the transdermal absorption preparation completed on the release liner 10, and the transdermal absorption preparation can be more easily applied to the skin.

Control Layer

As shown in the third embodiment of the transdermal absorption preparation precursor 52, a control layer 7 may be laminated on the adhesive layer 4 in the transdermal absorption preparation precursor of the present invention.

In the transdermal absorption preparation precursor of the present invention, the control layer 7 controls the release amount and release rate of the drug contained in the drug-containing layer 3 in a given transdermal absorption preparation to be produced, when the drug is released from the surface of the drug-containing layer 3 to the adhesive layer 4 due to spreading diffusion. It exerts a barrier function against free diffusion.

When a transdermal absorption preparation having a laminate structure in which a control layer is laminated on a drug-containing layer is stored, transfer and adsorption of the drug contained in the drug-containing layer to the control layer proceed and affect drug releaseability during administration. In the transdermal absorption preparation precursor of the present invention, the drug-containing layer 3 and the control layer 7 are separately formed on the release liner 10, and the drug-containing layer 3 and the control layer 7 are separately preserved (stored), thereby preventing transfer and adsorption of the drug contained in the drug-containing layer to the control layer. When the drug is administered to the skin, a transdermal absorption preparation having a given laminate structure is completed on the release liner 10 by laminating the control layer 7 on the drug-containing layer 3, whereby stable drug releaseability can be obtained irrespective of drug storage conditions.

Examples of the control layer 7 include paper, non-woven fabric, woven fabric, perforated plastic film and the like. As long as a drug dissolves in the material, any non-porous plastic film (e.g., polyethylene film, polypropylene film, ethylene/vinyl acetate copolymer film) may be used. However, when a non-porous plastic film is used, the drug release rate from the drug-containing layer may decrease, which in turn may decrease the effective utilization ratio of the drug in the drug-containing layer. Therefore, preferably, a perforated plastic film, particularly a porous plastic film, is preferably used. The thickness of the porous plastic film is not particularly limited. To reduce an uncomfortable feeling (feeling of stiffness) when applying to the skin surface, a porous plastic film having a thickness of 100 μm or below is preferably used.

Specific examples of the porous plastic film include those made from a material such as polyethylene, polypropylene, polytetrafluoroethylene, ethylene/vinyl acetate copolymer, vinyl acetate/vinyl chloride copolymer, plastic vinyl chloride, polyurethane, polyvinylidene chloride, polyester or the like.

From the aspects of control of drug release, the porous plastic film preferably has an average pore size of 0.01-2.0 μm. The porosity is generally 20-95%, though it is not limitative.

In the transdermal absorption preparation precursor of the present invention, the control layer 7 is laminated on the adhesive layer 4. Therefore, a transdermal absorption preparation that controls the amount of drug release from the drug-containing layer 3 and the release rate thereof, ensures sustained transdermal absorption of the drug in the body, and suppresses skin irritation due to the drug can be obtained with ease.

The plane area of the control layer 7 is not particularly limited. It may be the same as that of the adhesive layer 4, a plane area larger than that of the adhesive layer 4 and protruding by not more than 3 cm from the periphery in the entire circumference of the adhesive layer 4, or may be smaller than that of the adhesive layer 4.

The thickness of the control layer 7 is preferably not less than 1 μm and not more than 100 μm from the aspects of good drug releaseability.

4. Fourth Embodiment

Figure 4:
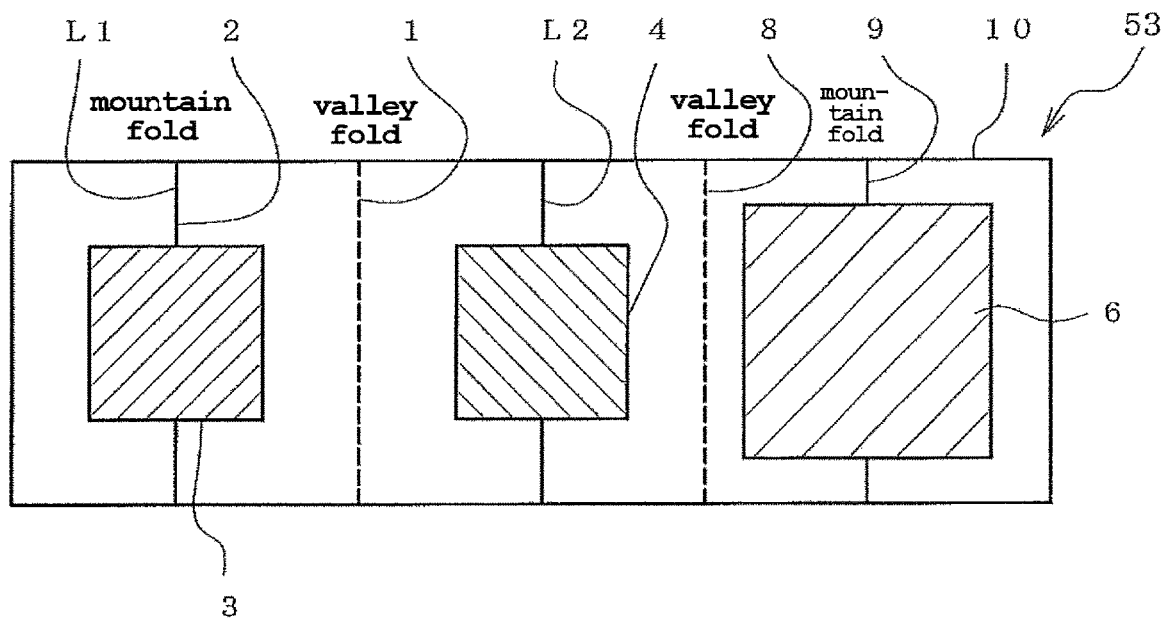
Figure 1:
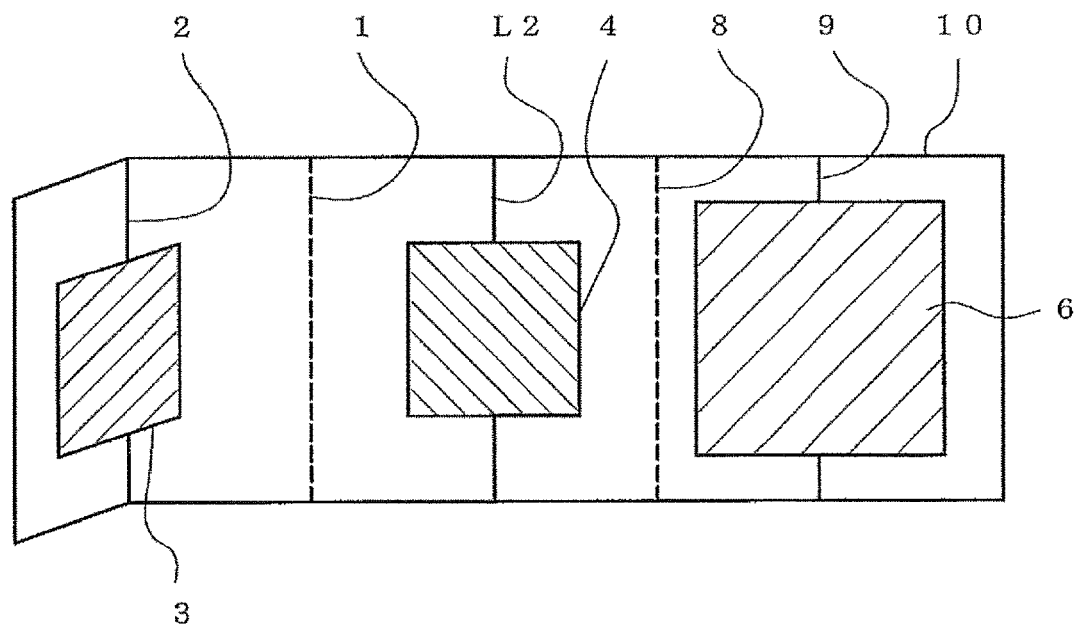
Figure 4:
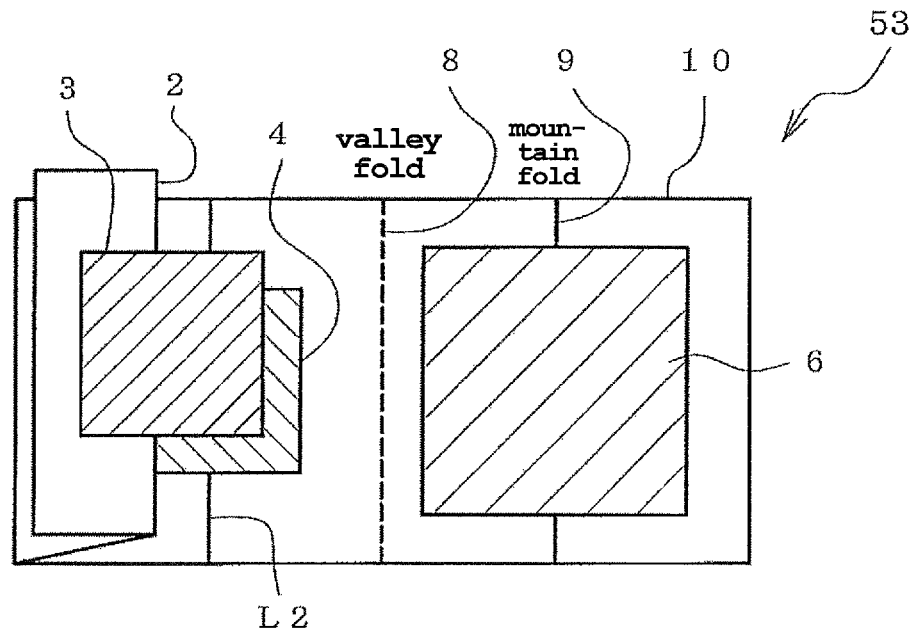
Figure 2:
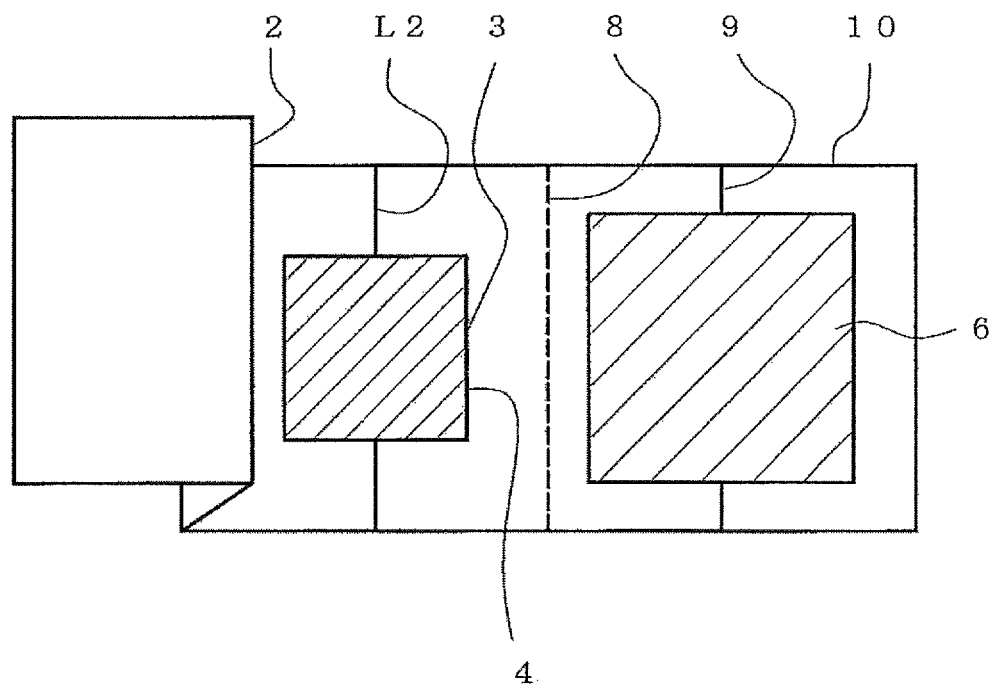

FIG. 4-1(A), FIG. 4-1(B), FIG. 4-2(A), FIG. 4-2(B), FIG. 4-3(A) and FIG. 4-3(B) are schematic drawings of one embodiment of the fourth embodiment of the transdermal absorption preparation precursor of the present invention, and FIG. 4-3(C) is a schematic drawing of a transdermal absorption preparation constructed using the transdermal absorption preparation precursor. In these Figures, the same symbols as in FIG. 2(A)-FIG. 2(E) show the same or corresponding parts.

In the transdermal absorption preparation precursor 53 of this embodiment, the second valley fold part 8 and the second mountain fold part 9 are further added to the release liner 10 in the transdermal absorption preparation precursor of the first to third embodiments to separately dispose, on the release liner 10, 3 layers to be contained in a given transdermal absorption preparation to be produced (transdermal absorption preparation to be completed). In this constitution, a second valley fold part 8 is formed at a position opposite from the first valley fold part 1 with the second base line L2 of the release liner 10 as a line of demarcation, a second mountain fold part 9 is further formed at a position opposite from the second base line L2 with the second valley fold part 8 as a line of demarcation, and the distance between the second valley fold part 9 and the second base line L2 is approximately equal to the distance between the second mountain fold part 9 and the second valley fold part 8. In the transdermal absorption preparation precursor 53 of this embodiment, the second base line L2 is a straight line recognizable by at least vision or touch, which is imparted by coloration, embossing and the like.

The transdermal absorption preparation precursor 53 of this embodiment can separately preserve a drug-containing layer 3 and an adhesive layer 4 (FIG. 4-1(A)). When the transdermal absorption preparation is applied to the skin, the first mountain fold part 2 is mountain folded (FIG. 4-1(B)), the first valley fold part 1 is valley folded (FIG. 4-2(A)), and the drug-containing layer 3 is laid (aligned) on the adhesive layer 4 while detaching the release liner 10 from the drug-containing layer 3, whereby the drug-containing layer 3 is laminated on the adhesive layer 4 (FIG. 4-2(B)). Thereafter, the second mountain fold part 9 is mountain folded (FIG. 4-3(A)), the second valley fold part 8 is valley folded (FIG. 4-3(B)), and the cover layer 6 is laid on the drug-containing layer 3 while detaching the release liner 10 from the cover layer 6, whereby the cover layer 6 is laminated on the drug-containing layer 3 and a transdermal absorption preparation having a laminate structure of cover layer 6/drug-containing layer 3/adhesive layer 4 is completed (FIG. 4-3(C)).

The transdermal absorption preparation precursor 53 in the above-mentioned embodiment has one drug-containing layer 3. A drug-containing layer may also be disposed under the cover layer 6 (drug-containing layer 3 covered by the cover layer 6 in FIG. 2(A)). Alternatively, a drug-containing layer may be disposed instead of the cover layer 6. In this way, a transdermal absorption preparation having a single drug-containing layer or a transdermal absorption preparation having a drug-containing layer as a two-layer laminate can be constructed on a release liner. As a result, a transdermal absorption preparation having desired drug content can be easily obtained according to the patient's symptoms. When a drug is also contained in the adhesive layer 4, transdermal absorption preparations in 3 patterns of drug content can be obtained easily.

In the transdermal absorption preparation precursor in the embodiment explained above, information of the order of mountain folding and valley folding is not attached on the release liner. By attaching such information, it is possible to construct a transdermal absorption preparation more certainly and efficiently. Examples of such information include characters, symbols and combinations of these, which are recognizable by at least vision or touch.

While the production method of the transdermal absorption preparation precursor of the present invention is not particularly limited, for example, a base line, a mountain fold part and a valley fold part for the precursor are formed on a release liner, layers (a drug-containing layer, an adhesive layer etc.) to be formed for the object transdermal absorption preparation precursor are formed on a different release liner, and the layers are transferred on the release liner for the precursor, whereby the transdermal absorption preparation precursor of the present invention is produced.

The transdermal absorption preparation precursor of the present invention can also be enclosed in a packaging bag together with a written matter indicating the order of mountain folding and valley folding of the release liner and the like and provided as a package.

The present invention is explained in more detail in the following by referring to Examples. The present invention is not limited by the following Examples, and can be practiced by making appropriate modifications within the range that can meet the above-mentioned and the below-mentioned gist. All of such modifications are encompassed in the technical scope of the present invention. In the following, "part" means "part by weight" unless particularly indicated.

EXAMPLE 1

(Preparation of Tramadol Octanoate)

Tramadol hydrochloride and sodium octanoate were dissolved in ultrapure water at equimolar amounts, ethyl acetate was further added and the mixture was stirred. Using a separatory funnel, the ethyl acetate layer was collected and washed with ultrapure water. Ethyl acetate was removed with an evaporator from the ethyl acetate layer after washing, methanol was further added and the solvent was removed. The residue after solvent removal was dried with a vacuum pump for about 16 hr to give a crystal of tramadol octanoate.

(Preparation of Acrylic Copolymer)

Under an inert gas atmosphere, 2-ethylhexyl acrylate (95 parts), acrylic acid (5 parts) and azobisisobutyronitrile (0.2 part) were subjected to solution polymerization in ethyl acetate at 60° C. to give an ethyl acetate solution of the above-mentioned copolymer.

(Production of Transdermal Absorption Preparation Precursor)

Methacrylic acid-methyl methacrylate copolymer ("EUDRAGIT L100" (manufactured by Evonik Rohm GmbH), glass transition temperature: 150° C., 20 parts) and tramadol octanoate (80 parts) were kneaded and extruded with heating in a biaxial hot melt extruder to give a mixture. An appropriate amount of the mixture was placed on a release-treated surface of a PET liner (thickness=75 μm), covered with a PET film (thickness=25 μm), and compression molded with a heat press into a sheet with a mixture thickness of 250 μm. An approximate square having a plane area of 10 cm$^2$ (height 32 mm×width 32 mm) and a circular arc with radius 5.3 mm (R=5.3 mm) applied to the four corners thereof was punched out to give a first laminate having a drug-containing layer.

An ethyl acetate solution of acrylic copolymer (34.7 parts as solid content), isopropyl myristate (65 parts) and trifunctional isocyanate ("CORONATE HL" (manufactured by Nippon Polyurethane Industry Co., Ltd.), 0.3 part as a solid content) as a crosslinking agent were added to an appropriate amount of ethyl acetate. The mixture was uniformly dissolved by sufficient mixing and stirring to give a coating solution. The obtained coating solution was applied to a release-treated surface of PET liner 1 (thickness=75 μm) to a thickness after drying of about 100 μm, dried and a release-treated surface of PET liner 2 (thickness=75 μm) was adhered to the adhesive surface. An approximate square having a plane area of 10 cm$^2$ (height 32 mm×width 32 mm) and a circular arc with radius 5.3 mm (R=5.3 mm) applied to the four corners thereof was punched out to give a second laminate having a skin adhesive layer.

A paper liner (long side 16 cm, short side 6 cm, thickness 100 μm) with a rectangular planar shape was prepared, wherein a position at which the long side of the release liner was bisected was the first valley fold part, a position 4 cm apart from (fold line of) the first valley fold part toward one of the short sides was the first mountain fold part (=the first base line), and a position 4 cm apart from (fold line of) the first valley fold part toward the other short side was the second base line.

The PET release liner of the first laminate was detached, and the drug-containing layer was adhered to the release-treated surface of the paper liner such that the center line of the drug-containing layer and the first base line were aligned. Then, the PET release liner 2 of the second laminate was detached and the skin adhesive layer was adhered to the release-treated surface of the paper liner such that the center line of the skin adhesive layer and the second base line were aligned, whereby a transdermal absorption preparation precursor I was obtained.

(Evaluation of Condition of Drug)

The transdermal absorption preparation precursor I was preserved at room temperature, and the drug-containing layer after 1 day, 2 days, 1 month, 6 months and 8 months of preservation was observed visually and under a polarization microscope (DP71 manufactured by OLYMPUS). As a result, the drug was not crystallized in the drug-containing layer at any time point of preservation and was confirmed to be in an amorphous state.

(Operability Evaluation)

In the transdermal absorption preparation precursor I, the PET release liner 1 covering the skin adhesive layer was detached, the first mountain fold part was mountain folded to detach one part of the drug-containing layer from the paper release liner, and the paper release liner was valley folded at the first valley fold part to laminate the drug-containing layer on the skin adhesive layer such that the first base line (=fold line of the first mountain fold part) is aligned with the second base line, whereby a transdermal absorption preparation was obtained.

It was confirmed that the drug in the drug-containing layer of the transdermal absorption preparation precursor I obtained above was maintained in an amorphous state even after preservation at room temperature for 8 months, and crystallization of the drug could be prevented. In the operability evaluation, moreover, the transdermal absorption preparation precursor I was free of adhesion deviation (displacement of adhering position) between the drug-containing layer and the skin adhesive layer, lamination was performed with ease, and a given transdermal absorption preparation could be obtained easily.

This application is based on a patent application Nos. 2017-90695 and 2018-19319 filed in Japan, the contents of which are incorporated in full herein.

The invention claimed is:

1. A transdermal absorption preparation precursor comprising a release liner, a first layer formed on the release liner and a second layer formed on the release liner,
the release liner comprising one first valley fold part, two first mountain fold parts, and a first base line and a second base line on one side and the other side apart from the first valley fold part as a line of demarcation and at an approximately equal distance from the first valley fold part, wherein each of the first base line and the second base line is a fold line of the first mountain fold part,
the first layer having a planar shape being disposed on the release liner such that the center line of the plane is positioned on the first base line, and
the second layer having a planar shape being disposed on the release liner such that the center line of the plane is positioned on the second base line,
wherein when the release liner is folded in mountain fold in the first mountain fold parts and folded in valley fold in the first valley fold part, one of the first layer and the second layer is placed on the other layer without being reversed, and one or both of the first layer and the second layer comprise(s) a drug.

2. The transdermal absorption preparation precursor according to claim 1, wherein one of the first layer and the second layer is a drug-containing layer and the other is an adhesive layer.

3. The transdermal absorption preparation precursor according to claim 2, wherein the adhesive layer comprises an additive.

4. The transdermal absorption preparation precursor according to claim 2, wherein a control layer is laminated on the adhesive layer.

5. The transdermal absorption preparation precursor according to claim 2, wherein the adhesive layer comprises a drug.

6. The transdermal absorption preparation precursor according to claim 2, wherein a substrate layer and/or a cover layer are/is laminated on the drug- containing layer.

7. The transdermal absorption preparation precursor according to claim 1, further comprising
a second valley fold part at a position opposite from the first valley fold part with the second base line of the release liner as a line of demarcation;
a second mountain fold part at a position opposite from the second base line with the second valley fold part as a line of demarcation; and
a third layer having a planar shape and disposed on the release liner such that the center line of the plane is positioned on a fold line of the second mountain fold part, wherein
the distance between the second valley fold part and the second base line is approximately equal to the distance between the second mountain fold part and the second valley fold part.

8. The transdermal absorption preparation precursor according to claim 7, wherein the third layer is a cover layer.

9. The transdermal absorption preparation precursor according to claim 7, wherein the third layer is a drug-containing layer.

10. The transdermal absorption preparation precursor according to claim 3, wherein a control layer is laminated on the adhesive layer.

11. The transdermal absorption preparation precursor according to claim 3, wherein the adhesive layer comprises a drug.

12. The transdermal absorption preparation precursor according to claim 3, wherein a substrate layer and/or a cover layer are/is laminated on the drug-containing layer.

13. The transdermal absorption preparation precursor according to claim 4, wherein a substrate layer and/or a cover layer are/is laminated on the drug-containing layer.

14. The transdermal absorption preparation precursor according to claim 5, wherein a substrate layer and/or a cover layer are/is laminated on the drug-containing layer.

15. The transdermal absorption preparation precursor according to claim 2, further comprising
a second valley fold part at a position opposite from the first valley fold part with the second base line of the release liner as a line of demarcation;
a second mountain fold part at a position opposite from the second base line with the second valley fold part as a line of demarcation; and
a third layer having a planar shape and disposed on the release liner such that the center line of the plane is positioned on a fold line of the second mountain fold part, wherein
the distance between the second valley fold part and the second base line is approximately equal to the distance between the second mountain fold part and the second valley fold part.

16. The transdermal absorption preparation precursor according to claim 3, further comprising
a second valley fold part at a position opposite from the first valley fold part with the second base line of the release liner as a line of demarcation;
a second mountain fold part at a position opposite from the second base line with the second valley fold part as a line of demarcation; and
a third layer having a planar shape and disposed on the release liner such that the center line of the plane is positioned on a fold line of the second mountain fold part, wherein
the distance between the second valley fold part and the second base line is approximately equal to the distance between the second mountain fold part and the second valley fold part.

17. The transdermal absorption preparation precursor according to claim 4, further comprising
a second valley fold part at a position opposite from the first valley fold part with the second base line of the release liner as a line of demarcation;
a second mountain fold part at a position opposite from the second base line with the second valley fold part as a line of demarcation; and
a third layer having a planar shape and disposed on the release liner such that the center line of the plane is positioned on a fold line of the second mountain fold part, wherein
the distance between the second valley fold part and the second base line is approximately equal to the distance between the second mountain fold part and the second valley fold part.

18. The transdermal absorption preparation precursor according to claim 5, further comprising
a second valley fold part at a position opposite from the first valley fold part with the second base line of the release liner as a line of demarcation;
a second mountain fold part at a position opposite from the second base line with the second valley fold part as a line of demarcation; and
a third layer having a planar shape and disposed on the release liner such that the center line of the plane is positioned on a fold line of the second mountain fold part, wherein
the distance between the second valley fold part and the second base line is approximately equal to the distance between the second mountain fold part and the second valley fold part.

* * * * *